United States Patent [19]
Miyata et al.

[11] Patent Number: 6,026,321
[45] Date of Patent: Feb. 15, 2000

[54] APPARATUS AND SYSTEM FOR MEASURING ELECTRICAL POTENTIAL VARIATIONS IN HUMAN BODY

[75] Inventors: Takashi Miyata; Noriyoshi Matsuo; Hitoshi Uchida; Naomi Sawada, all of Shizuoka; Yutaka Tomita, Kanagawa, all of Japan

[73] Assignee: Suzuki Motor Corporation, Shizuoka, Japan

[21] Appl. No.: 09/050,989

[22] Filed: Mar. 31, 1998

[30] Foreign Application Priority Data

Apr. 2, 1997  [JP]  Japan  .................................. 9-099762
Dec. 25, 1997  [JP]  Japan  .................................. 9-367137

[51] Int. Cl.⁷ ...................................................... A61B 5/04
[52] U.S. Cl. ........................................... 600/546; 128/903
[58] Field of Search ................................... 600/546, 407; 128/903

[56] References Cited

U.S. PATENT DOCUMENTS

| | | |
|---|---|---|
| 3,646,606 | 2/1972 | Buxton et al. . |
| 4,522,211 | 6/1985 | Bare et al. . |
| 5,168,874 | 12/1992 | Segalowitz . |
| 5,203,330 | 4/1993 | Schaefer et al. . |
| 5,255,677 | 10/1993 | Schaefer et al. . |
| 5,269,302 | 12/1993 | Swartz et al. . |
| 5,318,039 | 6/1994 | Kadefors et al. . |
| 5,368,042 | 11/1994 | O'Neal et al. . |
| 5,450,845 | 9/1995 | Axelgaard ............................... 600/382 |
| 5,579,781 | 12/1996 | Cooke ..................................... 128/903 |

FOREIGN PATENT DOCUMENTS

| | | |
|---|---|---|
| 62202805 | 12/1987 | Japan . |
| 6349135 | 3/1988 | Japan . |
| 2283354 | 11/1990 | Japan . |
| 8196516 | 8/1996 | Japan . |

OTHER PUBLICATIONS

"Precision, Low Power Instrumentation Amplifier", published in Mar. 1994 by Burr–Brown Corporation.

"Development of an Active Electrode with an Amplifier for Surface Electromyogram", by Suzushi Nishimura and Yutaka Tomita, Collected Monographs of Automatic Measuring Control Society, vol. 29, No. 12, pp. 1474–1476 (1993) along with an English Abstract.

*Primary Examiner*—William E. Kamm
*Assistant Examiner*—Carl H. Layno
*Attorney, Agent, or Firm*—Greenblum & Bernstein, P.L.C.

[57] ABSTRACT

An apparatus for measuring potential variations in the human body, comprising: a pair of conductors, an attachment patch for attaching the conductors to the measurement sites; an amplifier that amplifies, as AC signals, the potential variations input from the conductors through connecting wires, a transmitter that transmits the amplified signals, a battery that supplies electric power to the amplifier and transmitter, a voltage-divider circuit that divides the voltage applied from the battery, and a compensator circuit that applies a voltage so divided to the amplifier as a reference voltage and, concurrently, rejects DC components input to the conductors, using the divided voltage as a reference voltage. Hence is provided a compact apparatus for measuring body signals such as myoelectric potentials, without restricting the movements of the test subject.

17 Claims, 11 Drawing Sheets

APPARATUS AND SYSTEM FOR MEASURING ELECTRICAL POTENTIAL VARIATIONS IN HUMAN BODY

BACKGROUND OF THE INVENTION

1. Field of the Invention

This invention concerns a human body signal measuring apparatus for measuring, by radio, such human body signals as myoelectric potentials (EMG=electromyography), oculo-electric potentials (EOG=electro-oculography), cardio-electric potentials (ECG=electrocardiography), and encephalo-electric potentials (EEG=electroencephalography). This body signal measuring apparatus can be employed not only in the field of medicine, but also in the fields of physiology (including kinematics) and psychology (as in studies of attention and arousal). It may also be attached to the driver of an automobile or other moving vehicle to measure the driver's conditions.

2. Description of the Related Art

Figure 13:
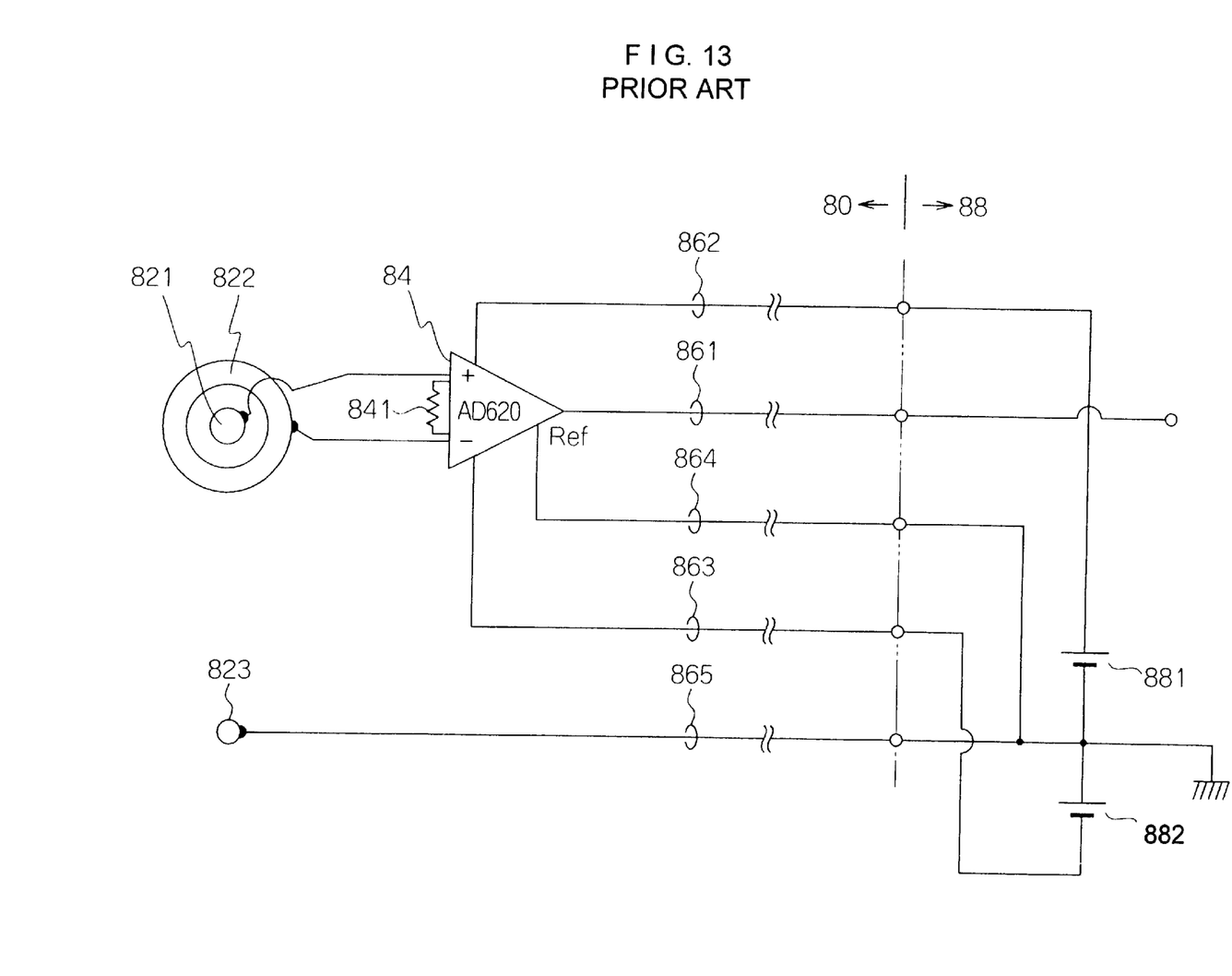
FIG. 13 is a circuit diagram of a conventional electromyograph.

FIG. 13 is a circuit diagram for a conventional electromyograph. This electromyograph will now be described with reference to this figure.

A conventional electromyograph 80 comprises a pair of detection electrodes (conductor) 821 and 822 for inputting myoelectric potentials, a ground electrode 832, an amplifier 84 for amplifying the myoelectric potentials input from the detection electrodes 821 and 822, a lead wire 861 for inputting the myoelectric potentials amplified by the amplifier 84 to a measuring instrument 88, lead wires 862 and 863 for supplying power to the amplifier 84, a lead wire 864 for supplying a reference voltage to the amplifier 84, and a lead wire 865 for connecting the ground electrode 823 to ground potential.

The detection electrodes 821 and 822 are arranged concentrically in order to measure myoelectric potentials without considering directionality. An IC called the "AD620BR," made by Analog Devices, is used in the amplifier 84. A resistor 841 is connected to this IC for setting the gain. ± power supplies 881 and 882 are built into the measuring instrument 88. The ± power supplies supply electric power to the amplifier 84 via the lead wires 862 and 863.

Myoelectric potentials may generally be thought of as AC signals referenced to 0 V. Therefore, in order to measure the myoelectric potentials, ± power supplies 881 and 882 are needed that are referenced to 0 V. In order to stabilize this reference potential at 0 V, the ground potential is applied to the skin in addition to the detection electrodes 821 and 822. This ground electrode and its connecting lead wire 865 are connected to the amplifier reference terminal. Thus the potential that constitutes the reference for amplification is always 0 V. When a potential variation having a DC component appears in the human body, this becomes a current that flows to ground from the ground electrode 823. Even supposing then that a DC component has been applied to the electrodes 821 and 822, that DC component will be applied to the ground electrode 823 at that time, whereupon the reference potential of the amplifier will also change. Thus the amplifier will perform amplification normally.

An electromyograph such as this is set forth, for example, in Nishimura and Tomita: *"Zofuku kino wo motsu kindenikei no shisaku* (Electromyograph with amplification functions)," *Keisoku Jido Seigyo Gakkai Ronbunshu* (Collected Monographs of Automatic Measuring Control Society), Vol. 29, No. 12, pp. 1474–1476 (1993).

With the conventional electromyograph 80, five lead wires 861–865 are required between it and the measuring instrument 88. Hence the movements of the test subject are limited in range to the length of the lead wires 861–865. In other words, the movements of the test subject are limited to simple, easy movements such as will not twist or pull out the lead wires 861–865.

For this reason, an electromyograph that operates by radio signals is desirable. Unfortunately, however, electromyographs that operate on radio signals are not known.

There are disclosures of techniques for transmitting heart rates by radio signals, for example in the laid-open patent applications H2-283354 [1990] and S63-49135 [1988]. These cardiotachometers can measure heart rate without restricting the movements of the test subject, by adding radio signal functions to the electrodes applied to the test subject. Compared to myoelectric potentials or oculo-electric potentials, however, the measurement of heart rate involves large potential differences, wherefore there is little need to consider noise produced by DC components in the human body.

Unlike cardiotachometry, when it comes to measuring such body potentials as heart potential, myoelectric potential, oculo-electric potential, and brain waves, the ground level has to be stabilized. When transmitting by radio, in particular, it is necessary to amplify potential variations in the human body. If the ground level is unstable, the amplifier will suffer saturation or other impairment, preventing the realization of radio transmissions.

In measuring myoelectric potentials, it is desirable to be able to measure potential variation while the test subject is moving. Radio transmission is thus most desirable in order to permit the test subject to move freely and to prevent noise interference due to the shaking of lead wires. In measuring myoelectric potentials, moreover, the smaller the electrodes are made, the more muscle types one can take measurements from. Hence it is desirable to do away with the ground electrode.

In view of these considerations, in designing an apparatus for measuring fluctuations in human body potentials, the following problems need to be resolved.

How to transmit the measured potential variations by radio in order to eliminate the effects of lead wire shaking and allow the test subject to move freely.

How to amplify body potential variations before transmission to facilitate transmitting weak body potential variations by radio.

It is necessary to supply the amplifier with a stable reference potential in order to amplify body potential variations. In order to do this amplifying, however, the DC components in the body and the variations in ground potential in the body need to be absorbed so that the amplifier will only amplify the body potential variations (AC components), thereby permitting a high amplification factor to be sustained.

Even if lead wires are eliminated so as not to restrict the movements of the test subject, the test subject's movements will nevertheless be restricted if the electrometer itself is large and/or heavy. In particular, an electrometer is needed of such size as will not hinder driving operations when attached to the driver of a motor vehicle.

In order to make the electrometer small, the battery needs to be limited to a single cell, and the use of a ground electrode eliminated, while still allowing the amplifier to function stably.

How to prevent crosstalk when multiple electrometers are attached to the test subject in multiple places and radio transmissions are done simultaneously, and how to maintain sufficient precision to permit comparing the potentials detected by the several electrometers, irrespective of differences in the performance of the electrometer amplifiers.

SUMMARY OF THE INVENTION

An object of the present invention, therefore, is to provide an electromyograph that is capable of measuring variations in weak body potentials such as myoelectric potentials without restricting the movements of the test subject.

Another object of the present invention is to detect body signals well while rejecting the effects of noise such as body DC components, even with a single battery cell, without having a common electrode.

Another object of the present invention is to stably maintain body signal measurement precision even in configurations in which body signals are amplified and transmitted by radio.

Another object of the present invention is to easily evaluate crosstalk conditions between transmissions of body signals from multiple electrodes.

Another object of the present invention is to be able to eliminate variation in the measurements of multiple electrometers, to make the reference for the body signals transmitted from the electrometers singular, and to make mutual comparisons of electrometer output values with a constant reference.

The present invention, therefore, is an apparatus for measuring body potential variation that comprises a pair of conductors, a bonding patch for attaching the conductors to the measurement sites, an amplifier for amplifying potential variations input from the conductors via connection wires, as AC signals, a transmitter for transmitting the amplified signals, a battery for supplying electric power to the amplifier and the transmitter, a divider circuit for dividing the voltage applied from the battery, and a compensator circuit for applying the a divided voltage as a reference voltage to the amplifier and, at the same time, rejecting DC components input to the conductors with the same divided voltage taken as the reference. By these means is provided an apparatus that is small in size for measuring body signals such as myoelectric potentials without restricting the movements of the test subject.

Thus, by adopting a radio signal mode to replace the conventional wire mode, lead wires are eliminated, and the test subject is allowed to move freely.

In the prior art, two power supplies were used, namely a + and a – power supply, and 0 V, or ground potential, in other words, was used as the reference voltage. In the present invention, however, by dividing a single constant DC voltage to obtain the reference voltage, one of the conventionally needed two power supplies and the ground electrode are made unnecessary. By amplifying the myoelectric potentials input from the detection electrodes and outputting these as radio signals, moreover, the lead wires required conventionally are rendered unnecessary, so the movements of the test subject—formerly restricted by lead wires—are freed up. In addition, the noise generated by the lead wires shaking or functioning as receiving antennas can be eliminated.

By adding to the compensator circuit a function for rejecting myoelectric potential noise input from the detection electrodes, moreover, the SN ratio can be improved, so that even weak myoelectric potential signals can be detected with greater precision than formerly.

When a plurality of electrometers is used simultaneously, furthermore, a mixer for mixing a reference signal of a predetermined frequency not contained in the body signal frequency band with the body signals input from the detection electrodes may be beneficially employed. When this is done, the frequency of the reference signal can be made different for each electrometer, and the reference signal frequency separated by a filter circuit will indicate a specific electrometer. Furthermore, if this reference signal is made a constant voltage, then the ratio between the voltages of the body signals and the reference signals separated by the filter circuit will be such as to eliminate the effects of fluctuation in amplification factor. This makes it possible to interpret potential variations measured by multiple electrometers against the same reference.

When the frequency of the reference signal is made different for each electrometer, in this manner, it is easy to verify which body signal is coming in from which electrometer by the frequency of the reference signal separated by the filter circuit in the receiver. It is also easy to evaluate crosstalk between the several electrometers because the reference signal frequency will be anomalous.

Furthermore, when the reference signal is made a constant voltage, it is possible to obtain high-precision body signals from which the effects of amplification factor fluctuation have been eliminated, by finding the ratio between the voltages of the body signals and the reference signals separated by the filter circuit.

When, moreover, the electrometers are specifically configured as laminated bodies, as compared to when they are made flat, the area occupied can be minimized, and the wiring distance between layers can also be minimized. When this is done, the problems caused by noise produced by wire shaking or wires functioning as antennas can be reduced. When measuring myoelectric potentials, moreover, the number of muscle types from which measurements are being taken can be increased by minimizing the areas occupied.

DESCRIPTION OF THE PREFERRED EMBODIMENTS

Figure 1:
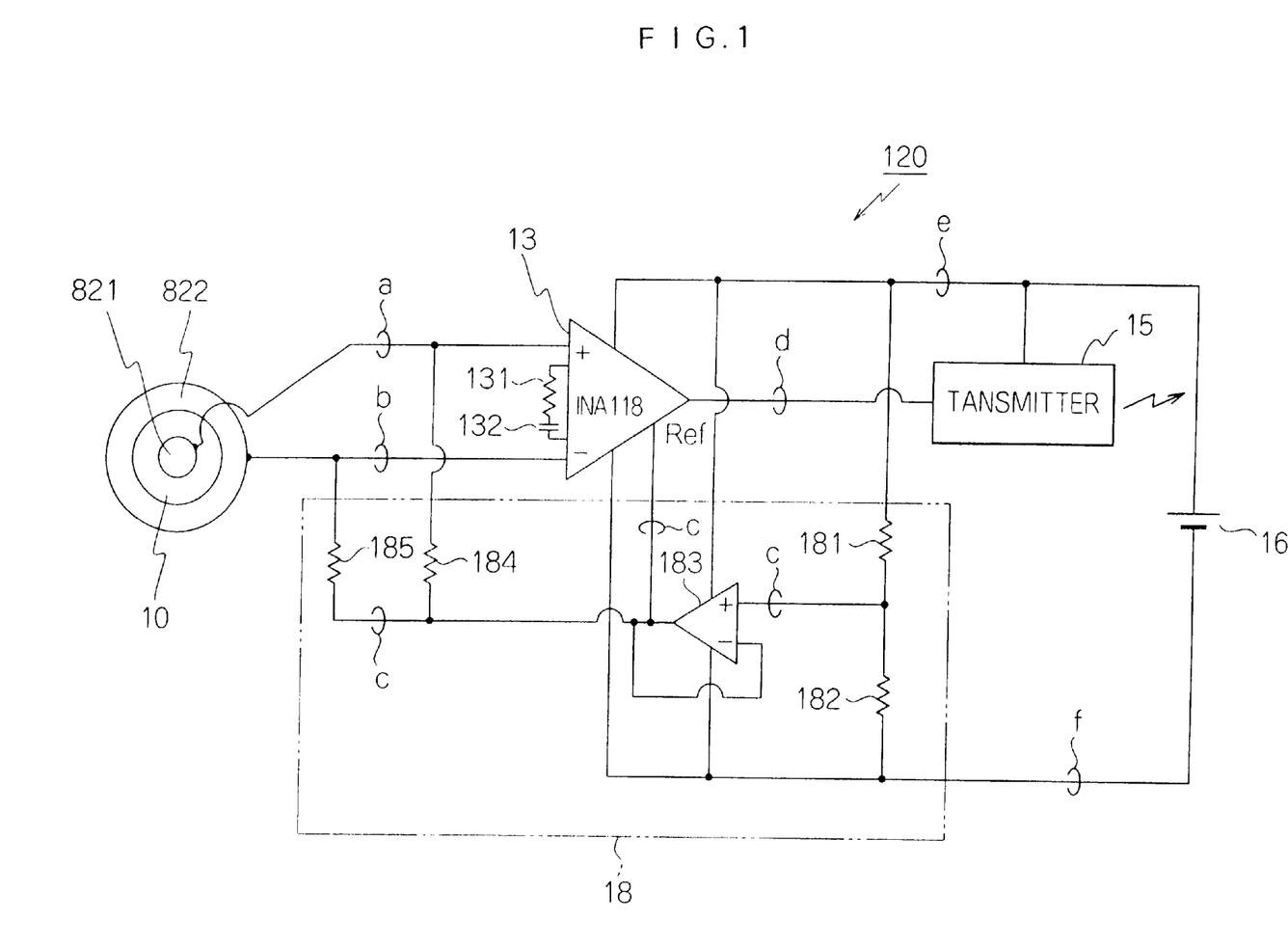
FIG. 1 is a circuit diagram for a first embodiment of an electromyograph to which the present invention pertains.
Figure 2:
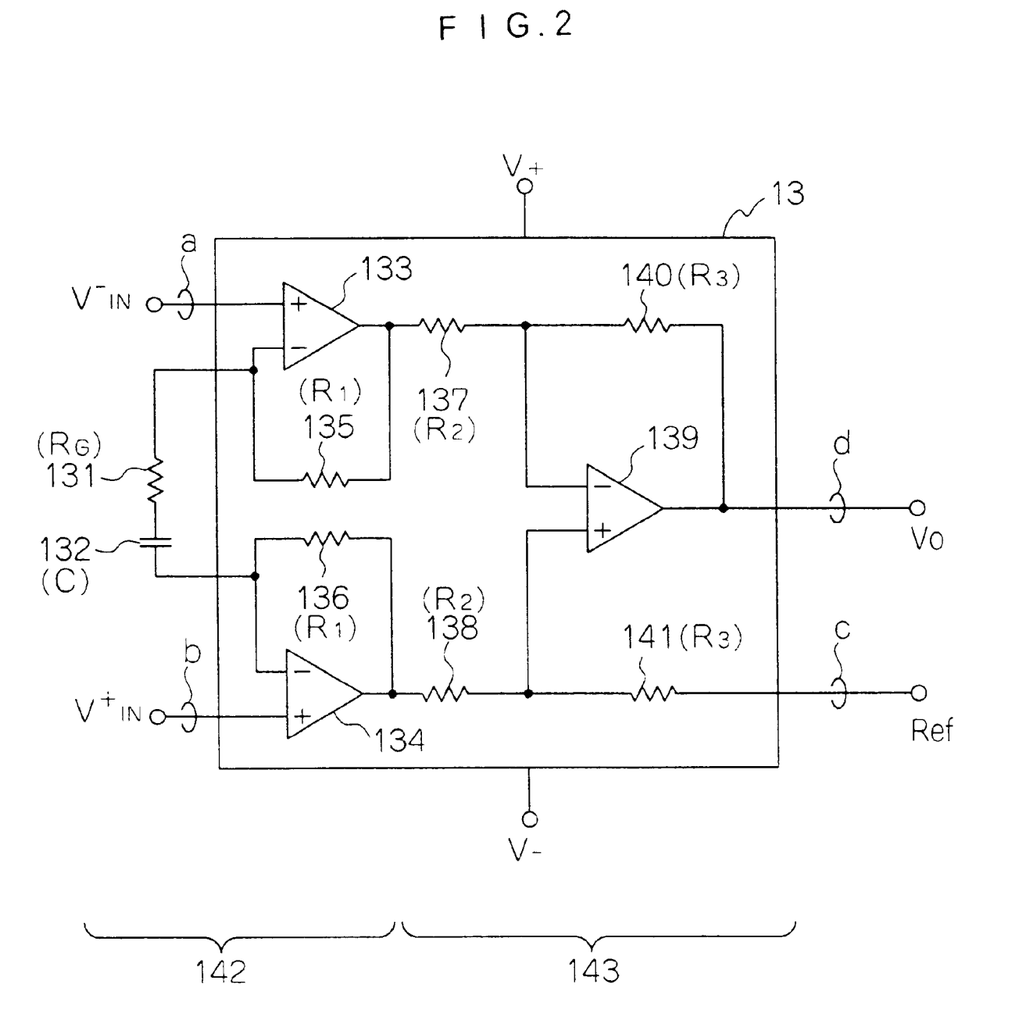
FIG. 2 is a circuit diagram for an example of an amplifier in the electromyograph diagrammed in FIG. 1.
Figure 3:
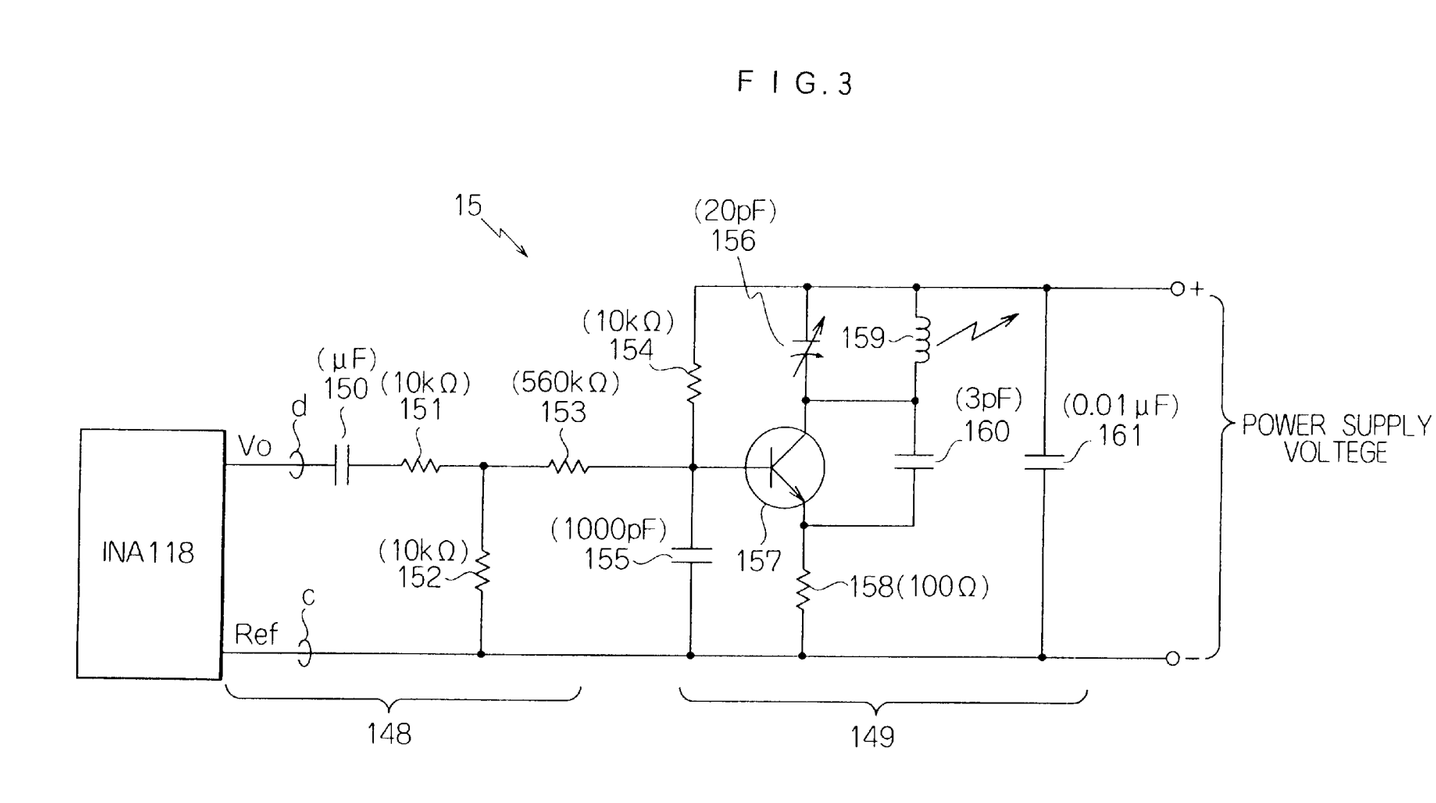
FIG. 3 is a circuit diagram for an example of a transmitter in the electromyograph diagrammed in FIG. 1.

FIG. 1 is a circuit diagram for a first embodiment of an electromyograph to which the present invention pertains; FIG. 2 is a circuit diagram for an example of an amplifier in the electromyograph diagrammed in FIG. 1; and FIG. 3 is a circuit diagram for an example of a transmitter in the electromyograph diagrammed in FIG. 1. The present invention will now be described with reference to these drawings. For the same elements as shown in FIG. 13, however, the same reference characters are used, and redundant descriptions are omitted.

The electromyograph 10 of this embodiment comprises a pair of detection electrodes 821 and 822 that input myoelectric potentials, an attachment patch 12 for securing the detection electrodes 821 and 822 to the skin, an amplifier 13 that amplifies the myoelectric potentials input from the detection electrodes 821 and 822 and outputs myoelectric potential signals, a transmitter 15 that outputs the myoelectric potential signals output from the amplifier 13, by radio, and a battery 16 that supplies electric power to the transmitter 15 and the amplifier 13. The battery 16 outputs only one constant DC voltage. A compensator circuit 18 is additionally provided for dividing a reference voltage from the constant DC voltage and outputting it to the amplifier 13.

In the example diagrammed in FIG. 2, an IC called the "INA118," made by the Burr-Brown Corporation, is used as the amplifier 13. To this IC is connected a resistor 131 and a capacitor 132 in a series circuit. This series circuit enables the realization of two functions, namely a function for setting the gain when amplifying the myoelectric potentials input from the detection electrodes 821 and 822, and the function of a high-pass filter for rejecting noise contained in the myoelectric potentials input from the detection electrodes 821 and 822 before they are amplified.

As diagrammed in FIG. 2, the amplifier 13 comprises a non-inverting amplifier 142 and a differential amplifier 143. The non-inverting amplifier 142 comprises an externally mounted resistor 131 and capacitor 132, operational amplifiers 133 and 134, and resistors 135 and 136, etc. The differential amplifier 143 comprises resistors 137 and 138 and operational amplifier 139. We express here the resistance of the resistor 131 by RG, the capacitance of the capacitor 132 by C, the resistance of the resistors 135 and 136 by R1, the resistance of the resistors 137 and 138 by R2, and the resistance of the resistors 140 and 141 by R3. Resistor 131 is for setting the gain. If the capacitor 132 is not present, that is, if the resistor 131 is shorted, then the gain G is given by $G = 1 + 50 (K\Omega)/RG$.

In this embodiment, the capacitor 132 is connected in series with the resistor 131, so the gain G is given by the following formula.

$$G = \{(RG + 2R1)j\omega C + 1\}/(j\omega CRG + 1)(R3/R2) \quad \text{(Formula 1)}$$

Here, if we let $R3 = R2$, $RG \ll R1$, and $\omega CR \gg 1$, then Formula 1 reduces to Formula 2.

$$|G| = 1 + 2R1/RG \quad (\omega \to \infty) \quad \text{(Formula 2)}$$

Then the cutoff frequency fC is given by formula 3.

$$fC = \frac{1}{2\pi CRG} \quad \text{(Formula 3)}$$

Referring once again to FIG. 1, the compensator circuit 18 comprises resistors 181 and 182 for dividing the constant DC voltage n V (which may be 3 V or 6 V, for example) of the battery 16, an operational amplifier 183 to function as a voltage follower for outputting the reference voltage n/2 V (which may be 1.5 V or 3 V, for example) obtained from the resistors 181 and 182 to the amplifier 13, and resistors 184 and 185 connected between the output terminal of the operational amplifier 181 and the ± input terminals of the amplifier 13, respectively. By connecting the resistors 184 and 185, respectively, between the output terminal of the operational amplifier 183 and the ± input terminals of the amplifier 13, the voltages from the detection electrodes 821 and 822 to the ± input terminals of the amplifier 13 are negatively fed back to the operational amplifier 183 via the resistors 184 and 185. Hence the noise is removed from the myoelectric potentials input from the detection electrodes 821 and 822. The rejected noise comprises DC components and common mode noise. The resistors 181, 182, 184, and 185 may have values, respectively, of 1 MΩ, for example.

When the battery has a voltage of 6 V, the voltage is 6 V at point e, so power will be supplied to the transmitter 15, operational amplifier 183, and amplifier 13 at a voltage of 6 V. Meanwhile, this voltage is divided by the resistors 181 and 182, so 3 V will appear at point c. The operational amplifier 183 is feeding back a negative output, so it will function to constantly maintain this voltage at 3 V. Thus the output of the amplifier 13 to the reference terminal and the positions where the resistors 184 and 185 are connected will always be at 3 V. The wire connecting this electrode and the amplifier is connected to the operational amplifier 183 through the resistors 184 and 185. For this reason, the reference voltage for the detection electrodes 821 and 822 will be the divided 3 V. An AC signal referenced against this 3 V is input to the amplifier 13.

Since the connecting wires between these electrodes and the amplifier are connected to the operational amplifier 183 through the resistors 184 and 185, the AC component will exhibit only very slight corruption, depending on the value of the resistors, and will not be input on the operational amplifier side. Meanwhile, the DC components above 3 V that appear on the electrodes 821 and 822 are shunted immediately to ground at point f by the negative feedback of the operational amplifier. Thus by dividing the voltage before inputting to the operational amplifier, a single battery may suffice. Also, because the detection electrodes 821 and 822 are connected to the operational amplifier through the resistors 184 and 185, the DC components on the detection electrodes are not input to the amplifier 13. And, by making the voltage-divided op-amp output the reference voltage for the amplifier, and, at the same time, the reference voltage for the detection electrodes, even if a DC component is input to the amplifier, the reference voltage will change simultaneously, wherefore that DC component will not become noise. Because this operational amplifier is provided with negative feedback, moreover, both the reference voltage to the amplifier 13 and the reference voltage for the detection electrodes will stabilize. By combining the operational amplifier 183 and the resistors 184 and 185 together with the voltage-divider circuit made up of the resistors 181 and 182, not only is a ground electrode rendered unnecessary, but it is possible to amplify body potential variations stably with a high amplification factor, without degrading the amplification factor by the effects of DC components and other common mode noise. Since it is possible, then, to amplify stably with a high amplification factor, the signals detected can be transmitted by radio. The body potential difference becomes the potential difference between the points marked c and d, which is input to the transmitter 15 as an AC signal.

The transmitter 15, as diagrammed in FIG. 3, may be an ordinary frequency-modulated (FM) oscillator circuit comprising a high-pass filter section 148 and an FM oscillator circuit section 149. The high-pass filter section 148 comprises a capacitor 150 and resistors 151–153. The FM oscillator section 149 comprises resistors 154 and 158, capacitors 155 and 160, a variable capacitor 156, and a coil 159. The capacitance of the variable capacitor 156 is varied to regulate the oscillation frequency. A wireless module in the "HRF-260 series" made by Hertz Radio Company, for example, may be used as the transmitter 15.

The attachment patch 12 may be an adhesive applied between the detection electrodes 821 and 822, for example.

The operation of the electromyograph 10 is next described. When the detection electrodes 821 and 822 are secured to the skin by the attachment patch 12, the myoelectric potentials produced by muscle activity are input from the detection electrodes 821 and 822. The myoelectric potentials so input are amplified by the amplifier 13, and then output to a measuring instrument (not shown) by radio signal from the transmitter 15. Thus the conventionally required lead wires are not needed, so that the test subject has freedom of movement instead of being restricted by the lead wires. Also, since constant DC voltage is divided and used as the reference voltage, by means of the battery 16 and compensator circuit 18, one of the two batteries conventionally required, and the ground electrode, are also made unnecessary. As a consequence, the electromyograph 10 can be implemented in a small light-weight package.

An embodiment is next described in which multiple electrometers 10 are employed to simultaneously measure potential variations at a plurality of sites on the test subject.

Figure 4:
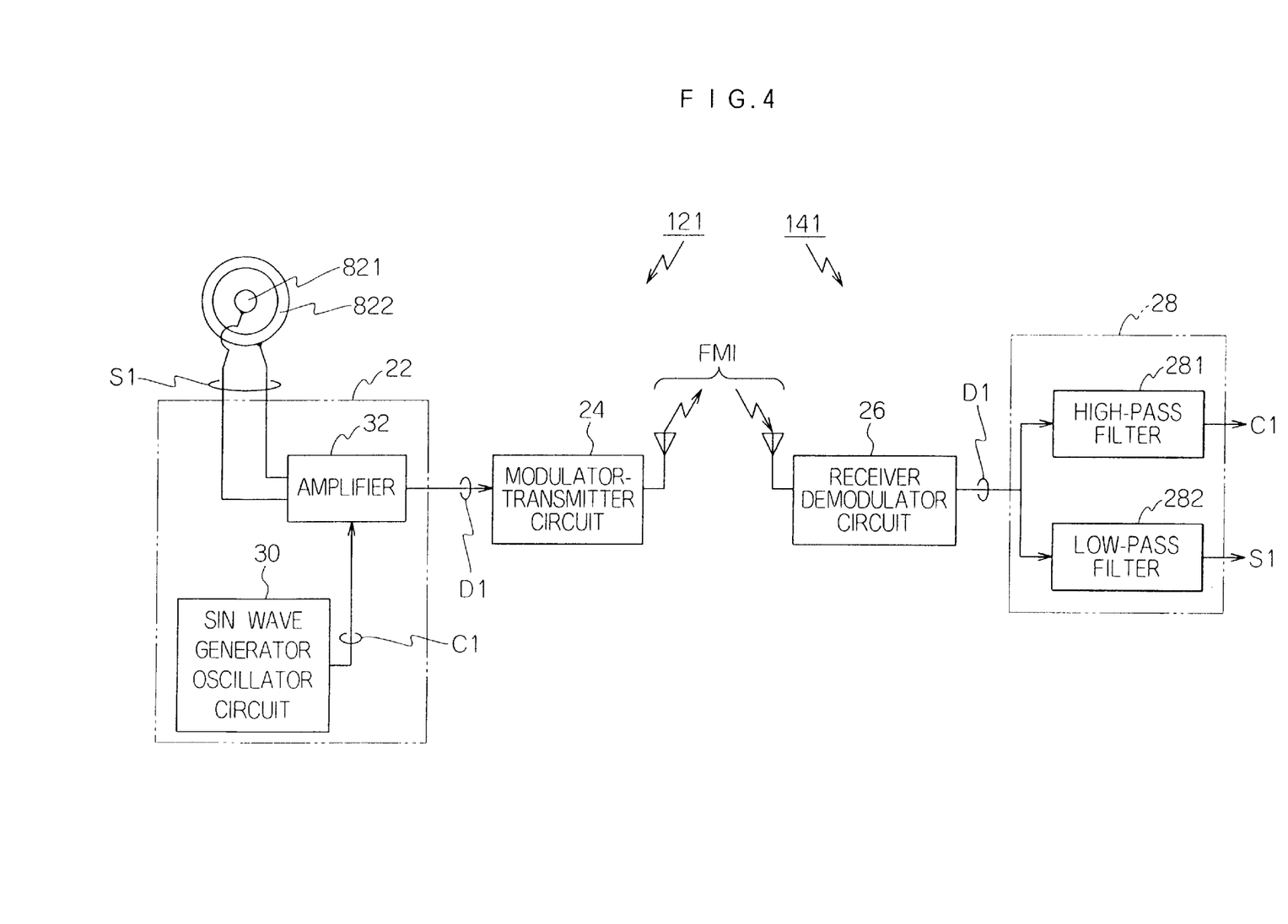
FIG. 4 is a simplified block diagram of a system for measuring body signals.
Figure 5:
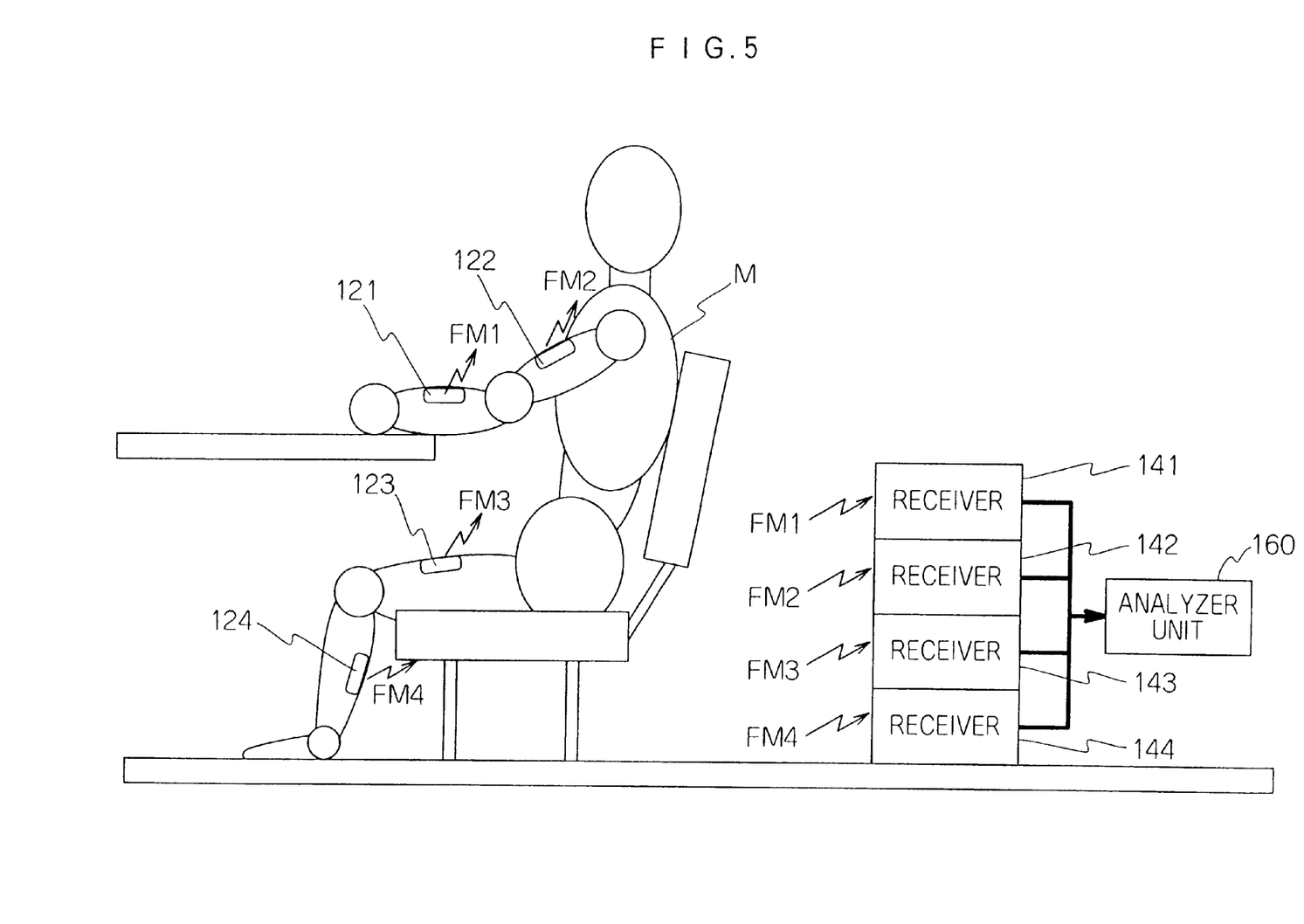
FIG. 5 is an explanatory diagram showing an example of the system diagrammed in FIG. 4 in use.

With reference to FIG. 4 and 5, the system for measuring body potential differences, in this embodiment, is a system for measuring myoelectric potentials, comprising four electrometers 121–124, secured to the skin of a test subject M, for sending body signals by radio, and four receivers 141–144 corresponding, respectively, to the four electrometers 121–124. The signals output by the receivers 141–144 are input to an analyzer unit 160. The analyzer unit 160 may be a computer.

The electrometer 121 comprises detection electrodes 822 and 821 for inputting body signals S1, a mixer-amplifier 22 that mixes a reference signal C1 having a frequency not included in the frequency band of the body signals S1 with the body signals S1, amplifies these, and outputs a detected signal D1, and a modulating transmitter 24 that modulates the detected signal D1 output from the mixer-amplifier 22 with a carrier wave FM1 that is of a different frequency for each of the electrometers 121–124 and transmits these. The receiver 141 comprises a receiver-demodulator circuit 26 that receives and demodulates the detected signal D1 transmitted from the electrometer 121, and a filter circuit 28 that takes the detected signal D1 output from the receiver-demodulator circuit 26 and separates it into body signals S1 and a reference signal C1.

The reference signal C1 has a different frequency for each of the electrometers 121–124, and is at a constant voltage. The electrometers 122–124 have the same configuration as the electrometer 121 excepting that the frequencies of the reference signals C2–C4 (not shown) and the carrier waves FM2–FM4 are different. The receivers 142–144 have the same configuration as the receiver 141 excepting that the frequencies just mentioned are different.

The detection electrodes 822 and 821 are arranged concentrically so that the myoelectric potentials can be measured without worrying about directionality. The mixer-amplifier 22 comprises a sine wave generator oscillator circuit 30 that generates the reference signal C1, and an amplifier 32 that mixes the reference signal C1 with the body signals S1, amplifies these, and outputs them as the detected signal D1. The modulator-transmitter 24 and the receiver-demodulator circuit 26 are ordinary devices comprising ICs for frequent modulation and frequency demodulation, respectively. The filter circuit 28 comprises a high-pass filter 281 that separates the reference signal C1 from the detected signal D1, and a low-pass filter 282 that separates the body signals S1 from the detected signal D1.

Figure 6:
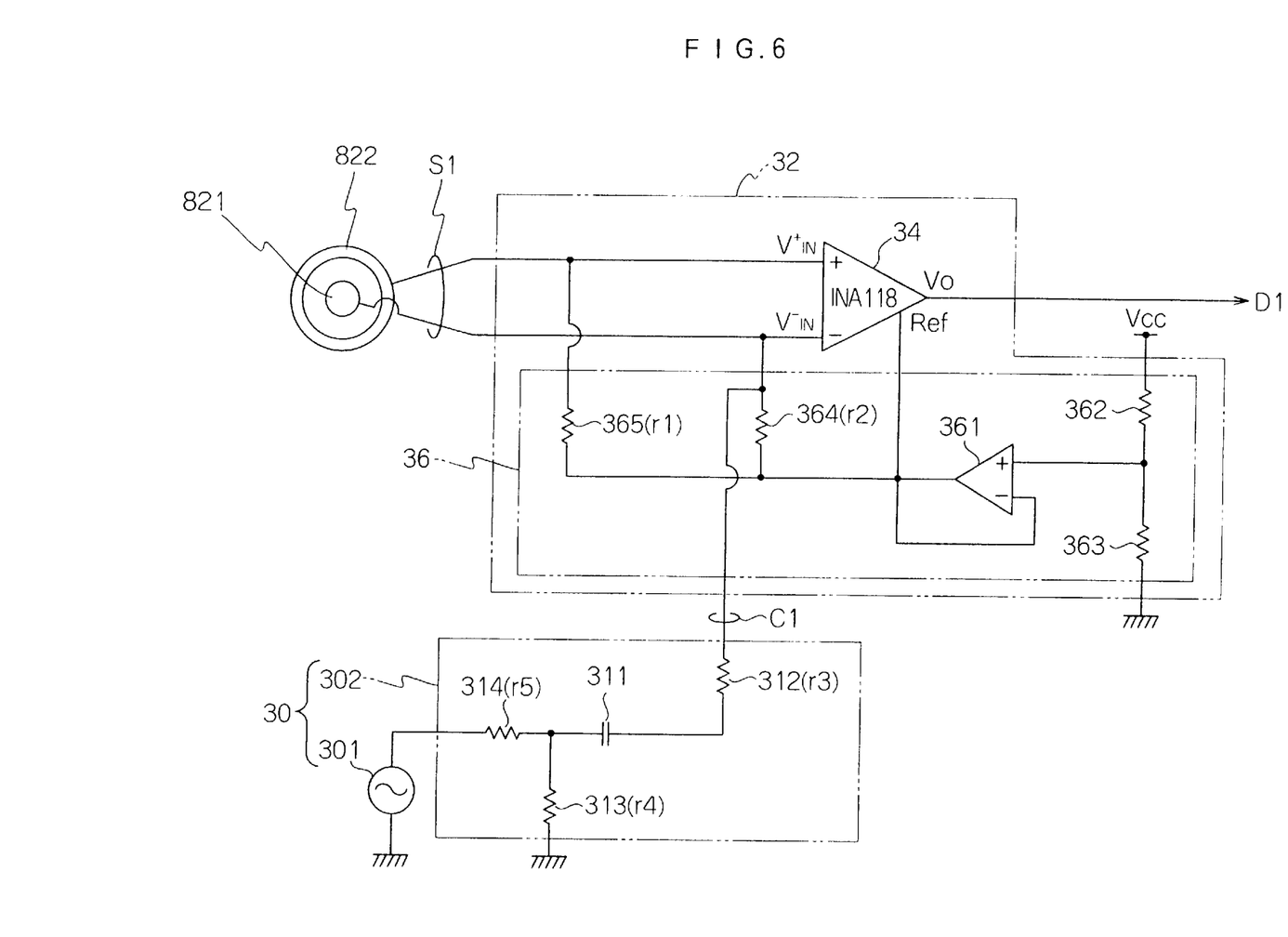
FIG. 6 is a circuit diagram of a sine wave oscillator circuit and a mixer-amplifier circuit in the system diagrammed in FIG. 4.
Figure 7:
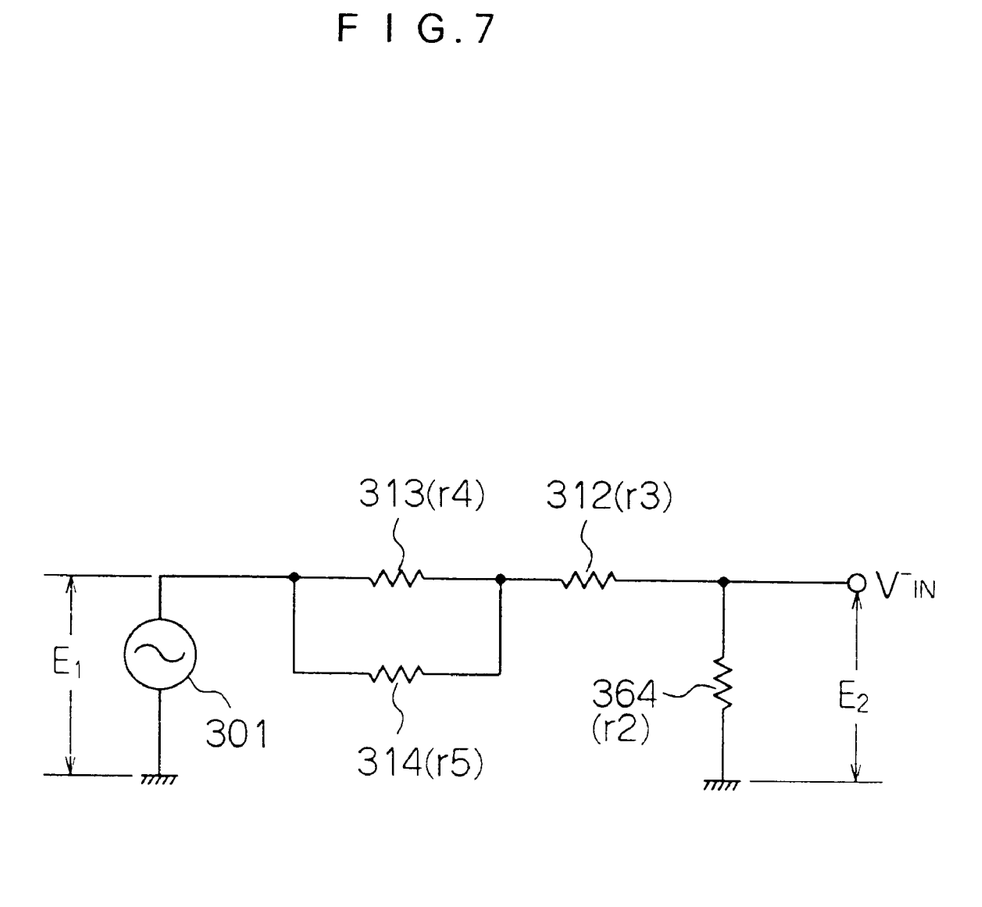
FIG. 7 is a circuit diagram for an equivalent circuit from the signal source to the amplifier in FIG. 6.

FIG. 6 is a circuit diagram of a sine wave generating oscillator circuit and a mixer-amplifier in the body signal measuring apparatus diagrammed in FIG. 4. FIG. 7 is a circuit diagram of an equivalent circuit from the signal source to the amplifier in FIG. 6. Further description will now be given, making reference to these drawings.

The mixer-amplifier 32 comprises an amplifier 34 and a compensator circuit 36. The power supply voltage Vcc is supplied from a battery (not shown). This is a single constant DC voltage. The compensator circuit 36, comprising an operational amplifier 361 and resistors 362–365, divides the supply voltage Vcc and outputs the voltage so divided to the amplifier 34 and operational amplifier 361. The compensator circuit 36 and amplifier 34 are configured as indicated in FIG. 1.

The sine wave oscillator circuit 30 comprises a signal source 301 that generates a sine wave that becomes the basis of the reference signal C1, and an amplitude attenuator circuit 302 that attenuates the sine wave generated by the signal source 301 to a prescribed amplitude. The signal source 301 may be an ordinary Wein bridge circuit, quadrature circuit, or crystal oscillator circuit, etc. The amplitude attenuator circuit 301 comprises a capacitor 311 and resistors 312–314.

The input impedances at the ± input terminals of the amplifier 34 both need to be made the same in order to avoid noise interference due to a drop in the CMRR (common mode rejection ratio). Accordingly, if we designate the values of the resistors 364, 365, 312, 313, and 314, respectively, as r1, r2, r3, r4, and r5 (where r5>>r4), then the resistance values are selected so as to satisfy the following relationship.

$$r1 = \{r2 \times (r3+r4)\} / \{r2 + (r3+r4)\} \quad \text{(Formula 4)}$$

If the output voltage from the signal source 301 is designated E1, then the input voltage E2 on the—input terminal of the amplifier 34 will be given by Formula 5.

$$E2 = r2/\{(r4//r5+r3)+r2\}] \times \{r4+(r4+45)\} \times E1 \quad \text{(Formula 5)}$$

By mixing this reference signal with the body signals, it becomes possible to evaluate the amplitudes of body signals measured by multiple electrometers using the same reference.

The operation of the body signal measuring apparatus 10 is next described, making reference to FIG. 4 and 5.

The electrometer 121 is first described. When the electrometer 121 is secured to the skin, body signals S1 constituted by myoelectric potentials that appear as a result of muscle activity are input from the detection electrodes 822 and 821. The body signals S1 so input are mixed with the reference signal C1 and amplified by the mixer-amplifier 22 to form the detected signal D1. This detected signal D1 is transmitted from the modulator-transmitter 24 on the carrier wave FM1 to the receiver 141 where it is restored by the receiver-demodulator circuit 26.

Here, if we designate the voltage and frequency of the body signals S1 as Vs1 and Fs1, respectively, and the voltage and frequency of the reference signal C1 as Vc1 and Fc1, respectively, the detected signal D1 will have a voltage of $\alpha(Vs1+Vc1)$ and the frequency components (Fs1, Fc1). If for the electrometers 122–124, similarly, we designate the voltages and frequencies of the body signals S2–S4 as Vs2–Vs4 and Fs2–Fs4, respectively, and the voltages and frequencies of the reference signals C2–C4 as Vc2–Vc4 and Fc2–Fc4, respectively, the detected signal D2–D4 will have voltages of $\alpha(Vs2+Vc2)$–$\alpha(Vs4+Vc4)$ and frequency components of (Fs2, Fc2)–(Fs4, Fc4), respectively. The body signals S1–S4 are myoelectric potentials, so the voltages will be in the mV range, and the frequencies from 5 Hz to 1 kHz. For the reference signals C1–C4, for example, we may have voltages Vc1–Vc4=10 mV, and frequencies of Fc1=2.0 kHz, Fc2=2.5 kHz, Fc3=3.0 kHz, and Fc4=3.5 kHz.

In the filter circuit 28 in the receiver 141, the cutoff frequency cf for the high-pass filter 281 and the low-pass filter 282 is selected so as to satisfy the relationship Fsmax<cf<Fcmin, where Fcmin is the minimum frequency of the reference signals C1–C4 and Fsmax is the maximum frequency of the body signals S1–S4. Accordingly, the voltage $\alpha Vc1$ and the frequency Fc1 will be obtained from the high-pass filter 281, and the voltage $\alpha Vs1$ and the frequency Fs1 will be obtained from the low-pass filter 282. The cutoff frequency cf will have the same values also in the receivers 142–144.

Now, the frequency Fc1 obtained from the high-pass filter 281 will indicate the electrometer 121, making it easy to verify that body signals S1 coming in from the electrometer 121 are being received. And, if the carrier waves FM2 and so on from the other electrometers 122 and so on appear as crosstalk on the carrier wave FM1 of the electrometer 121, this will result in a beat note with the mixing of the other frequencies Fc2 and so on with the frequency Fc1, so that crosstalk can be easily evaluated. In the event that crosstalk occurs as a result of setting the carrier frequency of the electrometer 121, etc., in error, that, similarly, can be easily evaluated.

In addition, from the voltage $\alpha Vs1$ obtained from the low-pass filter 282, the voltage $\alpha Vc1$ obtained from the high-pass filter 281, and the known voltage Vc1 of the reference signal C1, the voltage Vs1 of the body signal S1 can be calculated, using Formula 6.

$$Vs1=Vc1\times(\alpha Vs1)/(\alpha Vc1) \qquad \text{(Formula 6)}$$

As is evident from Formula 6, the effects of fluctuations in the amplification factor $\alpha$ have been eliminated from the value of the voltage Vs1.

Figure 8:
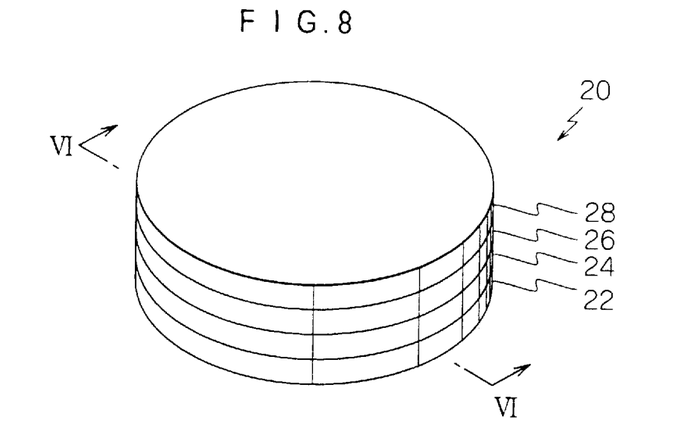
FIG. 8 is a diagonal view of one form of an electrometer.

The morphology of the electromyograph is next described, making reference to FIG. 8–11. FIG. 8 is a diagonal view thereof, FIG. 9 a bottom view, FIG. 10 a vertical cross-sectional view in the VI—VI plane in FIG. 8, and FIG. 11 a diagram of the configuration when an antenna is attached.

Figure 9:
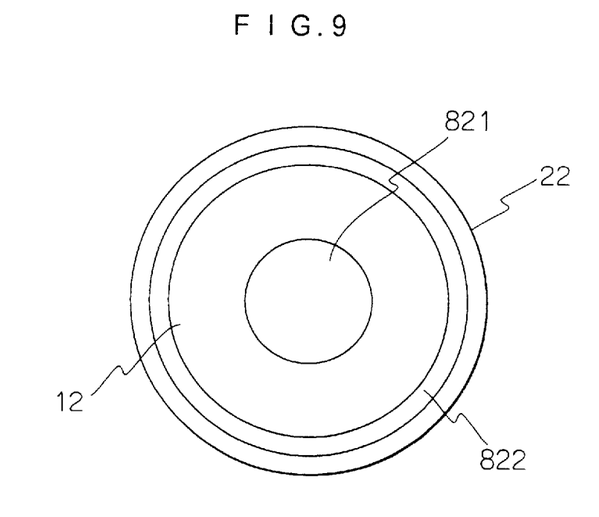
FIG. 9 is a bottom view of the electrometer depicted in FIG. 8.
Figure 10:
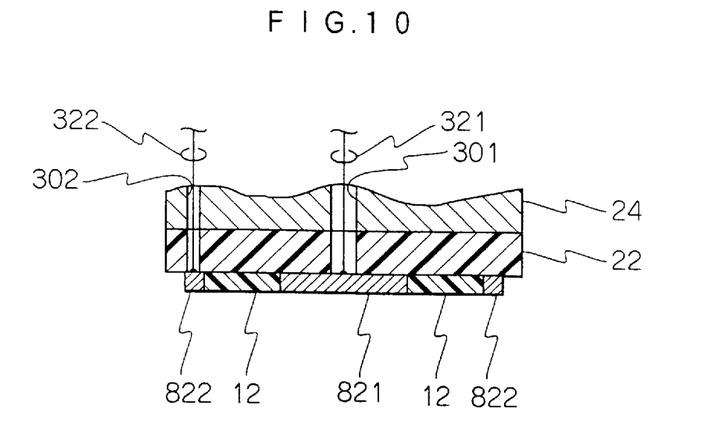
FIG. 10 is a vertical cross-sectional view in the VI—VI plane of FIG. 8.

The electrometer 20 in this embodiment comprises a first plate 22 on the lower surface of which are provided detection electrodes 821 and 822 and an attachment patch 12, a second plate 24 that is laminated to the upper surface of the first plate 22 and which becomes ground potential for the amplifier 13, transmitter 15, and compensator circuit 18, a third plate 26 that is laminated to the upper surface of the second plate 24 and in which is accommodated the electronic circuit board for the amplifier 13, transmitter 15, and compensator circuit 18, and a fourth plate 28 that is laminated to the upper surface of the third plate 26 and in which is accommodated the battery 16. The diameters of all of the circular plates 22, 24, 26, and 28 are the same. The plates 22 and 24 are provided with through holes 301 and 302 through which are passed lead wires 321 and 322 for connecting the detection electrodes 821 and 822 and the amplifier 13.

With the plates 22, 24, 26, and 28 laminated into a four-ply structure, the area occupied is minimized, as compared to when a flat configuration is used, and the wiring distances between the layers are also minimized. As a result, the electrometer 20 can be made both small and light in weight. Also, when the area occupied is minimized, measurements can be taken from more types of muscles.

Figure 11:
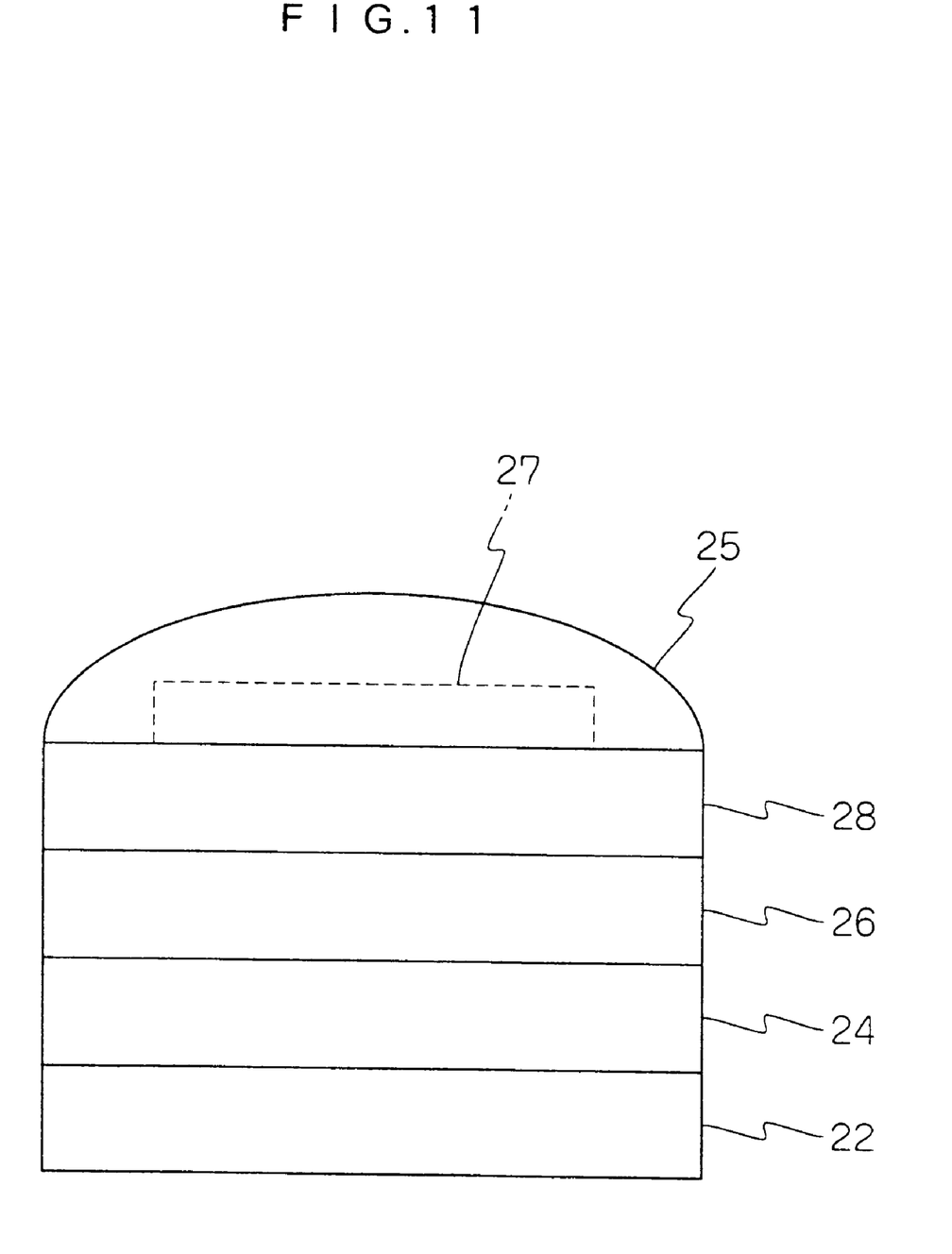
FIG. 11 is a front elevation of the electrometer depicted in FIG. 8 but with a cover provided.

As depicted in FIG. 11, a cover 25 can also be laminated on to protect the transmitter antenna 27. When that is done, there is no danger of the antenna getting caught on something when the test subject moves around. This cover will have a diameter of from 3 to 5 cm and a height of about 1 cm. In the example in which the frequency of the reference signal is altered for each electrometer, a number can be applied to the antenna cover 25 to serve as a reference corresponding to the number of the receiver.

In the example depicted in FIG. 11, no switch is provided. By configuring the device so that it is charged without providing a switch, a smaller size and lighter weight can be realized.

Figure 12:
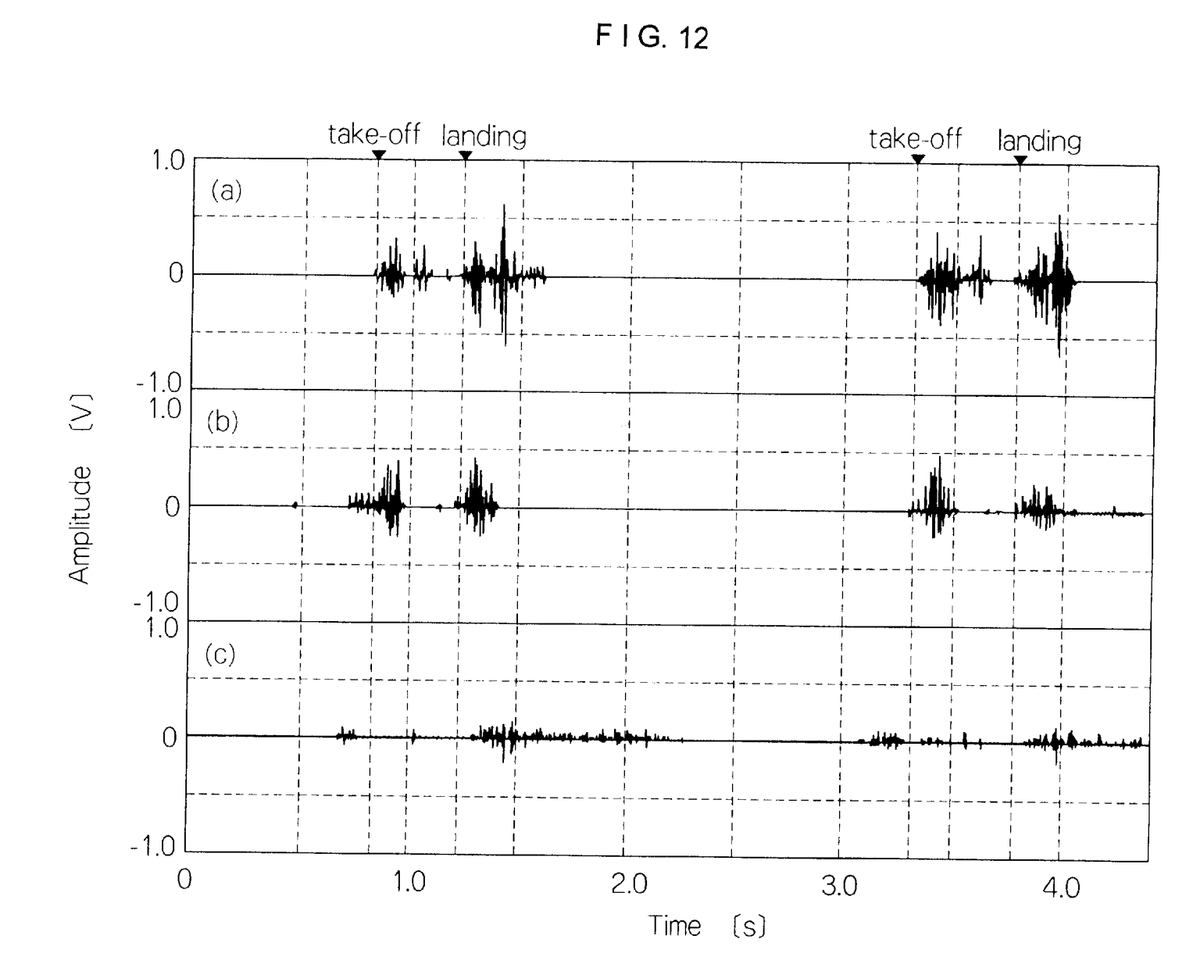
FIG. 12 shows EMG waveforms derived by electrometer.

FIG. 12 shows EMG waveforms derived by the wireless electrodes on jumping movement (a) right gastroenemius muscle, (b) left gastrocnemius muscle, (c) right tibialis anterior muscle. In FIG. 12, base voltage is change from 3 V to 0 V for display.

The invention may be embodied in other specific forms without departing from the spirit or essential characteristic thereof. The present embodiments is therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 9-099762 (filed on Apr. 2, 1997) and 9-367137 (filed on Dec. 25, 1997) including specification, claims, drawings and summary are incorporated herein by reference in its entirety.

What is claimed is:

1. An apparatus for measuring electric potential variations in the human body, comprising:

an attachment patch for attaching conductors to the measurement sites;

an amplifier for amplifying potential variations input from said conductors through connection wires;

a transmitter for transmitting the amplified signals;

a battery for supplying electric power at a constant DC voltage to said amplifier and transmitter;

a voltage-divider circuit to divide the voltage applied from said battery; and a compensator circuit that applies a voltage so divided to said amplifier as a reference voltage and, the compensator circuit rejects DC components input to said conductors, using said divided voltage as a reference voltage;

said compensator circuit including an operational amplifier having an output which directly feeds back to a negative terminal of said operational amplifier, said output further being connected to both positive and negative terminals of said amplifier.

2. The apparatus for measuring electrical potential variations in the human body according to claim 1, wherein said voltage-divider circuit comprises:

two resistors of equal value connected, respectively, to the positive and negative sides of said power supply; and connecting wires for connecting between said two resistors and reference terminal of said amplifier.

3. The apparatus for measuring electrical potential variations in the human body according to claim 1, wherein said battery supplies electric power at a voltage of 6 V to said transmitter, voltage-divider circuit, and amplifier.

4. The apparatus for measuring electrical potential variations in the human body according to claim 1, wherein said compensator circuit comprises a voltage follower that negatively feeds back output to reference terminal of said amplifier.

5. The apparatus for measuring electrical potential variations in the human body according to claim 1, wherein said compensator circuit comprises:

resistors connected, respectively, to each of a pair of conductors; and a connecting wire that makes an imaginary short at a prescribed voltage;

wherein said connecting wire is connected to:
reference terminal of said amplifier;
said resistor connected to one of said pair of conductors; and
resistor connected to other of said pair of conductors.

6. The apparatus for measuring electrical potential variations in the human body according to claim 1 wherein said amplifier comprises an externally attached resistor for setting gain; and a capacitor connected in series with said resistor.

7. An apparatus for measuring electrical potential variations in the human body, comprising:

a pair of conductor means;

attachment means for attaching said conductors to measurement sites;

amplifying means for amplifying potential variations input from said conductors through conducting wires, as AC signals;

transmission means for transmitting amplified signals;

battery means for supplying electric power to said amplifier and transmitter;

voltage-divider means for dividing voltage applied from said battery; and compensator means that applies a voltage so divided to said amplifying means as a reference voltage and that, concurrently, rejects DC components input to said conductor means, using said divided voltage as a reference voltage, said compensator means including an operational amplifier having an output that feeds back directly into its negative terminal, and said output being connected to positive and negative inputs of said amplifying means.

8. The apparatus for measuring electrical potential variations in the human body according to claim 7, wherein said compensator means comprising:

means for stabilizing the reference voltage to said amplifier;

means for rejecting DC components input to said conductors.

9. A system for measuring electrical potential variations in the human body, comprising:

multiple electrometers that are secured to the skin and that transmit body signals by radio; and multiple receivers corresponding, respectively, to said electrometers; wherein each of said electrometers comprises:

detection electrodes for inputting body signals;

a mixer-amplifier that mixes a reference signal of a constant voltage with body signals input from said detection electrodes, said reference signal having a frequency not contained in frequency band of those body signals, and that amplifies these as a detected signal; and a modulator-transmitter that modulates and transmits said detected signal output from said mixer-amplifier with a carrier wave having a frequency that is different for each of said electrometers; and each of said receivers comprises:

a receiver-demodulator circuit that receives and restores said detected signals from said electrometers; and a filter circuit that separates said detected signals output from said receiver-demodulator circuit into said body signals and said reference signal.

10. The system according to claim 9, wherein said electrometers have identifying labels that correspond with the frequency of the reference signal for each electrometer; and said receivers have identifying labels related to said identifying labels that correspond with said frequency of said reference signal for each of said electrometers.

11. The system according to claim 9, further comprising a first plate on the lower surface of which are provided detection electrodes and said attachment patch; a second plate that is laminated to the upper surface of said first plate and which becomes ground potential for said amplifier, etc.; a third plate that is laminated to the upper surface of said second plate and which accommodates electronic circuit board for said amplifier, etc.; and a fourth plate that is laminated to the upper surface of said third plate and which accommodates said battery.

12. The system according to claim 11, wherein said first through fourth plates have circular flat surfaces.

13. The system according to claim 12, wherein said circular forms have a diameter of 30–50 mm; and said first through fourth plates each have a height of 0.7–15 mm.

14. The system according to claim 11, further comprising an antenna connected to said transmitter circuit; and a cover that is provided at top of said fourth plate and which protects said antenna.

15. An apparatus for measuring electrical potential variations in the human body, comprising:

an attachment patch for attaching conductors to the measurement sites;

an amplifier for amplifying potential variations input from said conductors through connection wires;

a transmitter for transmitting the amplified signals;

a battery for supplying electrical power at a constant DC voltage to said amplifier and transmitter;

a voltage-divider circuit to divide the voltage applied from said battery;

a compensator circuit that applies a voltage so divided to said amplifier as a reference voltage and, the compensator circuit rejects DC components input to said conductors, using said divided voltage as a reference voltage;

said voltage-divider circuit including two resistors of equal value connected, respectively, to the positive and negative sides of said power supply; and said voltage-divider circuit including connecting wires for connecting between said two resistors and a reference terminal of said amplifier.

16. An apparatus for measuring electrical potential variations in the human body, comprising:

an attachment patch for attaching conductors to the measurement sites;

an amplifier for amplifying potential variations input from said conductors through connection wires;

a transmitter for transmitting the amplified signals;

a battery for supplying electrical power at a constant DC voltage to said amplifier and transmitter;

a voltage-divider circuit to divide the voltage applied from said battery;

a compensator circuit that applies a voltage so divided to said amplifier as a reference voltage and, the compensator circuit rejects DC components input to said conductors, using said divided voltage as a reference voltage;

said compensator circuit comprising:

resistors connected, respectively, to each of a pair of conductors; and a connecting wire that makes an imaginary short at a prescribed voltage;

wherein said connected wire is connected to:

a reference terminal of said amplifier;

said resistor being connected to one of said pair of conductors; and a resistor connected to the other of said pair of conductors.

17. An apparatus for measuring electrical potential variations in the human body, comprising:

an attachment patch for attaching conductors to the measurement sites;

an amplifier for amplifying potential variations input from said conductors through connection wires;

a transmitter for transmitting the amplified signals;

a battery for supplying electrical power at a constant DC voltage to said amplifier and transmitter;

a voltage-divider circuit to divide the voltage applied from said battery;

a compensator circuit that applies a voltage so divided to said amplifier as a reference voltage and, the compensator circuit rejects DC components input to said conductors, using said divided voltage as a reference voltage;

wherein said amplifier comprises an externally attach resistor for setting gain, and a capacitor connected in series with said resistor.

* * * * *